(12) United States Patent
Yaegashi et al.

(10) Patent No.: US 7,223,873 B2
(45) Date of Patent: May 29, 2007

(54) PROCESS FOR PREPARING AMINES

(75) Inventors: Keisuke Yaegashi, Osaki (JP); Masafumi Mikami, Osaka (JP)

(73) Assignee: Daisco Co., Ltd, Osaka-Fu (JP)

( * ) Notice: Subject to any disclaimer, the term of this patent is extended or adjusted under 35 U.S.C. 154(b) by 282 days.

(21) Appl. No.: 11/079,167

(22) Filed: Mar. 15, 2005

(65) Prior Publication Data
US 2005/0222430 A1    Oct. 6, 2005

(30) Foreign Application Priority Data
Mar. 30, 2004    (JP)    ............................. 2004-097461

(51) Int. Cl.
*C07D 27/12*    (2006.01)
*C07C 29/68*    (2006.01)

(52) U.S. Cl. ...................... 548/542; 564/463

(58) Field of Classification Search ................ 548/542; 564/463
See application file for complete search history.

(56) References Cited

FOREIGN PATENT DOCUMENTS

| | | |
|---|---|---|
| GB | 924042 | 4/1963 |
| JP | B 4-10452 | 2/1992 |
| JP | 5-255204 | 10/1993 |
| JP | 2001-220372 | 8/2001 |
| WO | 97/43256 | 11/1997 |

OTHER PUBLICATIONS

Mehler, T. et al., "Enantioselective addition of diethylzinc to aromatic aldehydes catalysed by chiral ligands derived from L-hydroxyproline", *Synthetic Communications*, vol. 23(19), pp. 2691 to 2699 (1993).
Hashimoto, M. et al., "A novel decarboxylation of α-amino acids. A facile method of decarboxylation by the use of 2-cyclohexen-1-one as a catalyst", *Chemistry Letters*, pp. 893 to 896 (1986).
Wallbaum, S. et al., "Decarboxylation of α-amino acids containing two and three stereogenic centers: a simple one-step procedure to prepare two optically active β-amino alcohols and a bicyclic pyrrolidine derivative", *Synthetic Communications*, vol. 24(10), pp. 1381 to 1387 (1994).
Pandey, G. et al., "Further Evidence on the PET Cyclization of α-Silylmethylamines Tethered with Non-activated Olefins: Demonstration by the Total Synthesis of (-)-Retronecanol." *Tetrahedron Letters*, vol. 37, No. 13, pp. 2285 to 2288 (1996).
Trybulski, E. et al., "The synthesis and structure activity relationships of enantiomerically pure hydroxylated oxotremorine derivatives" *Bioorganic and Medicinal Chemistry Letters*, vol. 2, No. 8, pp. 827 to 832 (1992).

*Primary Examiner*—Kamal A. Saeed
(74) *Attorney, Agent, or Firm*—Wenderoth, Lind & Ponack, L.L.P.

(57) ABSTRACT

A process for preparing an amine which comprises in preparing an amine by decarboxylating an α-amino acid under heating in a high boiling liquid polymer having average molecular weight 200 to 6000, and directly recovering this amine by distillation in the same reaction system, namely in one pot.

6 Claims, No Drawings

PROCESS FOR PREPARING AMINES

BACKGROUND OF THE INVENTION

The present invention relates to a process for preparing an amine which is useful as an intermediate for synthesis of medicines, agrochemicals, etc.

The processes for preparing an amine by decarboxylating an α-amino acid have been studied from of old, but there are many methods which have problems not desirable for industrial application such as requiring for drastic heating for long term, or catalyst such as a dangerous peroxide.

Recently the methods which solve the above problems and may be useful for the industrial method have been reported.

For example, (1) the amine is prepared by decarboxylating an α-amino acid under heating in the presence of a vinyl ketone as catalyst in a solvent such as cyclohexanol, etc., (Japanese Patent Publication B4-10452), (2) the amine is prepared by decarboxylating an α-amino acid under heating in the presence of a monoaryl ketone as catalyst in a solvent such as cyclohexanol, etc., (Japanese Patent Publication A 5-255204), (3) the amine is prepared by decarboxylating cis-3-hydroxy-L-proline or trans-3-hydroxy-L-proline in the absence of catalyst in a solvent such as cyclohexanol, etc., (WO97/43256), and (4) the amine is prepared by heating an α-amino acid and an aliphatic saturated ketone followed by hydrogenation (Japanese Patent Publication 2001-220372).

DETAILED DESCRIPTION OF THE INVENTION

By the way, many of amines prepared by decarboxylating α-amino acids are unstable for heating. For example, in regard to 3-hydroxypyrrolidine prepared by decarboxylating 4-hydroxyproline, the decrease of its weight begins at around 50° C. and the drastic thermolysis is observed at around 120° C. according to its thermogravimeteric analysis (TG/DTA). As be seen from the thermoanalysis, it is difficult to isolate the unstable product prepared by decarboxylating an α-amino acid by the usual procedure such as concentration of the reaction mixture followed by distillation and therefore, the dangerous procedures are accompanied with it.

Therefore, the safe and reproducible isolation method of amines prepared by decarboxylating an α-amino acid has been desired. However, the following problems have not been solved by above mentioned methods, yet.

Namely, in regard to the methods (1) to (3), the isolation and purification is carried out by forming the object compound into its hydrochloride and crystallized after decarboxylating, the steps are complex and troublesome, and that the isolation and purification of the object compound in free amine has not been established. In regard to the method (4), the isolation and purification of the object compound in free amine is carried out by adding water to the reaction mixture, extracting the object compound, concentrating the water layer and then distilling in vacuo, but it is not said that this conventional procedure solves the problem on above mentioned thermolysis. Therefore, it is not still enough for the measures to isolate amines safely and reproducibly.

The present inventors have been extensively studied to solve the above problems and as a result, have found the safe and reproducible method for isolating thermolysistic amines prepared by decarboxylating an α-amino acid in form of free amines. Thus the present invention has been completed.

Namely, the present invention relates to a process for preparing an amine which comprises in preparing an amine by decarboxylating an α-amino acid under heating in a high boiling liquid polymer having average molecular weight 200 to 6000, and directly recovering said amine by distillation from the same reaction system, namely in one pot.

As the present invention consists in using a high boiling point liquid polymer as a solvent and is not necessary for removal of the solvent, it becomes simple to recover the object compound by distillation and the stability of the object compound is promoted even under heating.

PREFERRED EMBODIMENTS FOR CARRYING OUT THE INVENTION

The α-amino acid used in this process is not limited as far as the amino group and the carboxyl group on the compound are present on the same carbon atom, and the amino group has at least one hydrogen atom.

For example, an α-amino acid having alkyl group or aryl group as a side chain such as alanine, leucine, isoleucine, valine, phenylglycine, phenylalanine, tyrosine, etc., a cyclic amino acid such as proline, hydroxyproline, pipecolic acid, etc. an α-amino acid having a functional group like carboxyl group, amino group, hydroxy group, mercapto group or methyl mercapto group such as aspargic acid, glutamic acid, lysine, ornithine, threonine, methionine, cysteine, triptophan, etc., and furthermore, a derivative thereof and an α-amino acid having other substituent are illustrated.

Therefore, when an α-amino acid has hydroxy group on a carbon atom other than the carbon atom at a position, the amine having hydroxy group on said carbon atom is obtained by decarboxylating reaction. For example, when the α-amino acid is 4-hydroxyproline, 3-hydroxypyrrolidine is obtained as an amine. Especially, when said carbon atom in the α-amino acid has asymmetric, the optically active corresponding amine is obtained by decarboxylating reaction.

The high boiling liquid polymer having average molecular weight 200 to 6000 used in this reaction may be at least one selected from poly $C_{1\ to\ 6}$ alkylene glycol, poly $C_{1\ to\ 6}$ alkylene glycol $C_{2\ to\ 7}$ fatty acid ester and poly $C_{1\ to\ 6}$ alkylene glycol $C_{1\ to\ 6}$ alkyl ether. Its fatty acid may be unsaturated. Polyethylene glycol and polypropylene glycol are especially preferable.

The decarboxylating reaction is carried out at 120° C. to 250° C., preferably at 140° C. to 170° C. The reaction is carried out at atmospheric pressure, but may be carried out at pressure. The reaction period is suitable selected depending on the reaction temperature, the reaction pressure, etc.

The reaction proceeds even without catalyst, but is accelerated by adding suitable catalyst in the reaction system. A vinyl ketone such as 2-cyclopenten-1-one, 2-cyclohexen-1-one, 2-cyclhepten-1-one, etc. is preferably illustrated as the catalyst. The amount is preferably 0.01 to 0.2 moles to the α-amino acid.

After the reaction, as the boiling point of the high boiling liquid polymer used as a solvent is higher than that of the produced amine, the conventional removal procedure of the solvent before distillation of the product is not required and therefore, the object amine in free form is obtainable by directly distillating the reaction mixture under reduced pressure in one pot.

In this reaction, the high boiling polymer is served not only as a solvent, but also as a stabilizer in distillation on high temperature and, therefore during the distillation procedure the amine is obtained without remarkable degradation.

The present invention is in detail explained by the following examples but the present invention should be limited by these examples.

The measurement of optical purity was conducted by HPLC (CHIRALCEL AS: Daicel Chemical) by benzoylation of hydroxy group of 3-pyrrolidinol.

EXAMPLE 1

(R)-3-Pyrrolidinol

To a 1 liter reaction vessel were added (4R)-hydroxy-L-proline (250 g, 1.907 mol), 2-cyclohexen-1-one (18.3 g, 0.1907 mol) and polyethylene glycol (750 mL; average molar weight 400), and the mixture was stirred under a stream of nitrogen gas at 150~160° C. After 10 hours, when the crystals were disappeared and the mixture became homogenous, the reaction was judged to be completed. By quantitatively analyzing by gas chromatography, the yield of (R)-3-pyrrolidinol was 89.3%. Then at the same temperature, the reaction solution was directly distilled under reduced pressure to give (R)-3-pyrrolidinol as a distilled portion of 100~120° C. (6~40 hPa) (120.4 g, yield: 72.5%, chemical purity: 99.6%, optical purity: 99.9% ee).

EXAMPLE 2

(R)-1-Amino-2-propanol

To a 500 mL reaction vessel were added L-threonine (10 g, 0.839 mol), 2-cyclohexen-1-one (8.07 g, 0.084 mol) and polyethylene glycol (300 mL, average molar weight 400), and the mixture was stirred under a stream of nitrogen gas at 150~160° C. After 72 hours, when the crystals were disappeared and the mixture became homogenous, the reaction was judged to be completed. By quantitatively analyzing by gas chromatography, the yield of (R)-1-amino-2-propanol was 80.6%. Then at the same temperature, the reaction solution was directly distilled under reduced pressure to give (R)-1-amino-2-propanol as a distilled portion of 54~62° C. (1~20 hPa) (44.4 g, yield: 70.4%, chemical purity: 99.0%, optical purity: 99.9% ee).

EXAMPLE 3

To an amino acid (0.100 mol) selected from leucine, isoleucine, valine, phenylglycine, lysine, methionine and triptophan, are added 2-cyclohexen-1-one (0.100 mol) and polyethylene glycol (three times as much as the amino acid). The mixture is stirred under a stream of nitrogen gas at 150~160° C. When the crystals are disappeared and the mixture becomes homogenous, the reaction is judged to be completed. Then at the same temperature, the reaction solution is directly distilled under reduced pressure. There is obtainable a corresponding amine.

COMPARATIVE EXAMPLE

To a 300 ml reaction vessel were added (4R)-hydroxy-L-proline (75.0 g, 0.572 mol), 2-cyclohexen-1-one (5.50 g, 57.20 moL) and cyclohexanol (225 mL), and the mixture was stirred under a stream of nitrogen gas at 150~160° C. After 8 hours, when the crystals were disappeared and the mixture became homogenous, the reaction was judged to be completed. By quantitatively analyzing by gas chromatography, the yield of (R)-3-pyrrolidinol was 83.3%. Then at 70–90° C. on a water bath, the reaction solution was concentrated under reduced pressure and the residue was analyzed by gas chromatography. As a result the yield of (R)-3-pyrrolidinol was 68.8% and the degradative ratio by concentration procedure was 14.5%. The residue was further distilled as a distilled portion of 100~116° C. (4 hPa) to give (R)-3-pyrrolidinol (28.75 g, isolation yield: 57.7%, chemical purity: 93.9%, optical purity: 99.9% ee).

The present invention is utilized for preparing for amines which are useful for intermediate for synthesis of a variety of medicines such as antibacterials, bronchodilators, etc., agrochemicals and physiologically active compounds.

The invention being thus described, it will be obvious that the same may be varied in many ways. Such variations are not to be regarded as a departure from the spirit and scope of the invention, and all such modification as would be obvious to one skilled in the art are intended to be included within the scope of the following claims.

What is claimed is:

1. A process for preparing an amine which comprises in preparing an amine by decarboxylating an α-amino acid under heating in a high boiling liquid polymer having average molecular weight 200 to 6000, and directly recovering said amine by distillation in the same reaction system.

2. The process for preparing an amine wherein the high boiling liquid polymer is at least one selected from poly $C_1$ $_{to\ 6}$ alkylene glycol, poly $C_{1\ to\ 6}$ alkylene glycol $C_{2\ to\ 7}$ fatty acid ester and poly $C_{1\ to\ 6}$ alkylene glycol $C_{1\ to\ 6}$ alkyl ether.

3. The process for preparing an amine wherein the high boiling liquid polymer is polyethylene glycol or polypropylene glycol.

4. The process for preparing an amine according to claim 1 wherein the α-amino acid has hydroxy group on a carbon atom other than the carbon atom at α position, and the amine has hydroxy group.

5. The process for preparing an amine according to claim 1 wherein the α-amino acid is 4-hydroxyproline, and the amine is 3-hydroxypyrrolidine.

6. The process for preparing an amine according to claim 1 wherein the α-amino acid has asymmetric carbon atom at other position than at a position of said α-amino acid, and the amine is an optically active amine.

* * * * *

UNITED STATES PATENT AND TRADEMARK OFFICE
CERTIFICATE OF CORRECTION

| | | |
|---|---|---|
| PATENT NO. | : 7,223,873 B2 | Page 1 of 1 |
| APPLICATION NO. | : 11/079167 | |
| DATED | : May 29, 2007 | |
| INVENTOR(S) | : Keisuki Yaegashi et al. | |

It is certified that error appears in the above-identified patent and that said Letters Patent is hereby corrected as shown below:

On the front page of the patent, in item (73), Assignee should be corrected from "Daisco Co., Ltd., Osaka-Fu (JP)" to --DAISO CO., LTD., Osaka-Fu (JP)--.

Signed and Sealed this

Twenty-first Day of August, 2007

JON W. DUDAS
*Director of the United States Patent and Trademark Office*